(12) United States Patent
Edmundson (10) Patent No.: US 10,538,455 B2
(45) Date of Patent: Jan. 21, 2020

(54) SYSTEM AND METHOD FOR STRAIGHTENING AND ELONGATING A GLASS CORE ROD

(71) Applicant: OFS Fitel, LLC, Norcross, GA (US)

(72) Inventor: Mark L Edmundson, Atlanta, GA (US)

(73) Assignee: OFS Fltel, LLC, Norcross, GA (US)

(*) Notice: Subject to any disclaimer, the term of this patent is extended or adjusted under 35 U.S.C. 154(b) by 185 days.

(21) Appl. No.: 15/790,469

(22) Filed: Oct. 23, 2017

(65) Prior Publication Data
US 2019/0119144 A1  Apr. 25, 2019

(51) Int. Cl.
C03B 23/00 (2006.01)
C03B 37/018 (2006.01)
C03B 23/045 (2006.01)

(52) U.S. Cl.
CPC ...... *C03B 37/01861* (2013.01); *C03B 23/045* (2013.01)

(58) Field of Classification Search
CPC ....... B23B 31/02; B23B 31/028; B23B 31/19; C03B 23/0093; C03B 23/045
USPC ............. 65/484, 485, 486, 533, 534, 537
See application file for complete search history.

(56) References Cited

U.S. PATENT DOCUMENTS

| | | | |
|---|---|---|---|
| 5,158,589 A * | 10/1992 | Curtis | C03B 23/045 228/44.5 |
| 6,359,400 B1 * | 3/2002 | Mueller | C03B 23/045 318/400.08 |
| 6,386,001 B1 * | 5/2002 | Shimizu | C03B 23/047 65/377 |
| 6,536,239 B1 * | 3/2003 | Mueller | C03B 23/045 249/100 |
| 6,742,363 B1 * | 6/2004 | Yamamura | C03B 23/047 65/377 |
| 2001/0008078 A1 * | 7/2001 | Pezet | C03B 23/045 65/511 |
| 2002/0053224 A1 * | 5/2002 | Charlton | C03B 23/043 65/382 |
| 2004/0129027 A1 * | 7/2004 | Sugiyama | C03B 23/045 65/105 |
| 2015/0007616 A1 * | 1/2015 | Fujii | C03B 37/01242 65/381 |

\* cited by examiner

*Primary Examiner* — Cynthia Szewczyk
(74) *Attorney, Agent, or Firm* — Lawrence D. Maxwell; Smith Tempel Blaha LLC (57) ABSTRACT

A lathe-based system may include chucks to retain a glass core rod, an arm, a slip joint, an actuator system, and a control system. The slip joint may couple the arm and a first chuck in fixed relation against relative axial motion with respect to an axis of rotation. The slip joint may also couple the arm and the first chuck in two-dimensionally movable relation with respect to a plane normal to the axis of rotation. The actuator system may be configured to two-dimensionally adjust a position of the first chuck in the plane. The control system may measure straightness of the glass core rod and control the actuator system in response to optical measurements of the straightness. In this manner, the system may straighten the glass core rod. The system may simultaneously elongate the glass core rod as it straightens the glass core rod.

21 Claims, 5 Drawing Sheets

SYSTEM AND METHOD FOR STRAIGHTENING AND ELONGATING A GLASS CORE ROD

BACKGROUND

In optical fiber manufacturing processes, fiber is drawn from a large-diameter glass structure known as a preform. Processes for making a preform include modified chemical vapor deposition (MCVD), outside vapor deposition (OVD) and vapor axial deposition (VAD). In MCVD, a hollow glass tube is collapsed inwardly to form a solid glass core rod to which cladding layers are then added. In OVD and VAD, particles are deposited on a glass core rod (also known as a seed rod or bait rod). In some types of processes for making a preform, it is important that the core rod be straight before the core rod is drawn or further elongated.

One method for straightening a glass core rod of the tubular type used in MCVD uses a rotating machine having a heating torch to soften the rod and a machine-vision feedback system to control the speed of rotation. The machine-vision feedback system measures the amount of bow in a rotating core rod and adjusts the speed of rotation to allow gravity to pull any upward bow in the core rod downwardly. While this method may be suitable for straightening the thin-walled tubes used in MCVD, it may be less suitable for straightening the solid (and thus more massive) core rods used in OVD and VAD.

Another method for straightening a glass core rod involves placing the core rod in a rotating machine, commonly referred to as a straightening lathe, and manually straightening the core rod. As a heating torch, which may be mounted on a carriage, is moved to different positions along the length of the core rod, an operator visually judges the straightness of the rotating core rod and presses a tool against portions of the rotating core rod judged to be bowed, until the operator judges the rod to be straight. After the core rod has been straightened, it may be transferred to a similar rotating machine, commonly referred to as an elongation lathe. The elongation lathe stretches or elongates the core rod while a heating torch, which may be mounted on a carriage, traverses the length of the core rod.

Some lathes of the types described above that are used to straighten or elongate core rods may include an optical measuring system comprising a laser and an optical sensor. The laser may direct a beam toward the core rod, and the optical sensor may receive the beam partially blocked by the core rod. Based on the optical sensor, the measuring system may display for the operator a measurement of the diameter or displacement of the core rod. The optical measuring system may be mounted on the same carriage as the torch.

SUMMARY

Embodiments of the invention relate to systems, devices, and methods for straightening a glass core rod. In some embodiments, the systems, devices, and methods may also elongate the glass core rod.

In one aspect, embodiments of a system may include a first chuck, an arm, a slip joint, an actuator system, and a control system. The first chuck may have a first chuck axis of rotation and is configured to retain a first end of a glass core rod in an orientation wherein a longitudinal axis of the glass core rod is substantially aligned with the first chuck axis of rotation. The arm may have an arm axis substantially aligned with the first chuck axis of rotation. The slip joint may couple the arm and the first chuck in fixed relation against relative axial motion with respect to the first chuck axis of rotation. The slip joint may also couple the arm and the first chuck in two-dimensionally movable relation with respect to a plane normal to the first chuck axis of rotation. The actuator system may be coupled to the arm and may be configured to two-dimensionally adjust a position of the first chuck in the plane. The control system may include an optical sensing system configured to measure straightness of the glass core rod. The control system may be configured to control the actuator system in response to optical measurements of the straightness of the glass core rod.

In another aspect, embodiments of a system may include a lathe, an arm, a slip joint, an elongation drive system, an actuator system, and a control system. The lathe may have a first chuck and a second chuck, each rotatably mounted with respect to a lathe axis of rotation, and configured to retain first and second ends of a glass core rod, respectively. The lathe may include a rotational drive system configured to rotate the first and second chucks. The arm may have an arm axis substantially aligned with the lathe axis of rotation. The slip joint may connect the arm and the first chuck in fixed relation against relative axial motion with respect to the lathe axis of rotation. The slip joint may also connect the arm and the first chuck in two-dimensionally movable relation with respect to a plane normal to the lathe axis of rotation. The elongation drive system may be coupled to the arm and configured to translate the first chuck along the lathe axis of rotation via the slip joint. The actuator system may be coupled to the arm and configured to two-dimensionally adjust a position of the first chuck in the plane via the slip joint. The control system may include an optical sensing system configured to measure straightness of the glass core rod. The control system may be configured to control the actuator system in response to optical measurements of the straightness of the glass core rod.

Embodiments of a method may include mounting a glass core rod in a lathe by retaining first and second ends of the glass core rod in first and second chucks, respectively. The method may further include rotating the glass core rod in the lathe. The method may also include measuring straightness of the glass core rod in the lathe using an optical sensing system. The method may further include heating a portion of the glass core rod in the lathe. The method may still further include two-dimensionally adjusting a position of the first chuck in a plane normal to the lathe axis of rotation using an actuator system and a control system responsive to measurements received from the optical sensing system.

Other devices, systems, methods, features, and advantages will be or become apparent to one of skill in the art upon examination of the following figures and detailed description. It is intended that all such additional systems, methods, features, and advantages be included within this description, be within the scope of the specification, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention.

DETAILED DESCRIPTION

Figure 1:
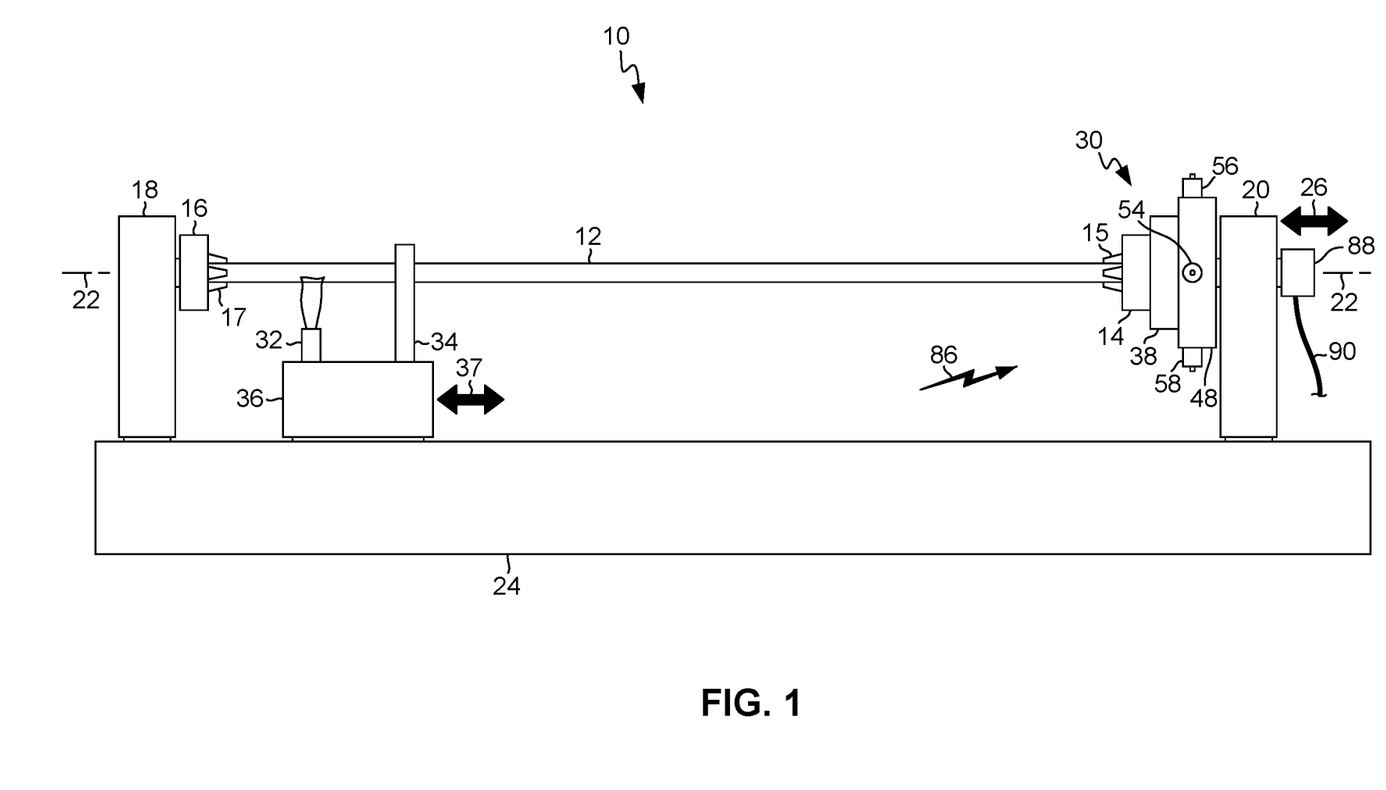
FIG. 1 is a side elevation view of a system for straightening and elongating a glass core rod, in accordance with exemplary embodiments of the invention.

As illustrated in FIG. 1, in an illustrative or exemplary embodiment of the invention, a system 10 is configured to rotate and otherwise work upon a glass core rod 12 (workpiece). System 10 thus may have characteristics of a lathe. The term "lathe" as used herein broadly means a machine in which a workpiece is rotated about an axis, without limitation as to the manner in which the workpiece may be worked upon. Accordingly, in system 10, a first chuck 14 is configured to retain a first end of glass core rod 12, and a second chuck 16 is configured to retain a second end of glass core rod 12. First and second chucks 14 and 16 may be of a conventional type known to be usable in glassworking lathes or similar lathes. For example, first and second chucks 14 and 16 may have sets of jaws 15 and 17, respectively, which an operator can adjust to clamp the ends of glass core rod 12. Second chuck 16 is coupled to a headstock 18, and first chuck 14 is coupled to a tailstock 20 in a manner that allows first and second chucks 14 and 16 to rotate about a lathe axis (of rotation) 22. The terms "headstock" and "tailstock" are used for convenience and do not indicate any spatial relationship to each other or other elements of system 10.

Headstock 18 and tailstock 20 are connected to a base 24. In the illustrated embodiment, the connection between headstock 18 and base 24 may be configured to fix headstock 18 in place. The connection between tailstock 20 and base 24 may be configured to allow tailstock 20 to traverse or move along base 24 parallel to lathe axis 22. Although tailstock 20 may move in a direction away from headstock 18 during a process (described in further detail below) of elongating glass core rod 12, tailstock 20 may be moveable in either direction, as indicated by the double-headed arrow 26. Although in the exemplary embodiment, headstock 18 may be mounted in a fixed position on base 24, in other embodiments both the headstock and tailstock may be moveable with respect to the base. Although not shown in FIG. 1, base 24 may contain a rotational drive system configured to rotate first and second chucks 14 and 16 through drive mechanisms in tailstock 20 and headstock 18, respectively. Similarly, although not shown in FIG. 1, base 24 may contain a translational or elongation drive system configured to move tailstock 20 in the directions indicated by arrow 26. Although not shown for purposes of clarity, base 24 may have a track or rail that tailstock 20 engages to guide or otherwise control the movement of tailstock 20.

System 10 includes a device 30 that couples first chuck 14 to tailstock 20 and functions in a manner described below to aid straightening glass core rod 12. System 10 also includes a torch 32 and an optical sensing system 34. Torch 32 may function in a manner described below to heat a portion of glass core rod 12, so that it softens and becomes workable (e.g., bendable). Optical sensing system 34 may be configured to measure the displacement of a portion of glass core rod 12. Measurements of such a distance may be used to estimate the straightness of glass core rod 12. The straightness of glass core rod 12 may be characterized in any way, such as deviations of points on glass core rod 12 from a line parallel to lathe axis 22 that would indicate glass core rod 12 is bowed, bent, etc. Torch 32 and optical sensing system 34 may be mounted on a carriage 36 configured to move in the directions indicated by the double-headed arrow 37. Carriage 36 may engage the above-referenced track or rail in base 24 to guide or otherwise control the movement of carriage 36. Although in the illustrated embodiment torch 32 and optical sensing system 34 are mounted on the same carriage 36, in other embodiments (not shown) such a torch and optical sensing system may be mounted on separate carriages that are independently movable. Also, although in the illustrated embodiment there is only a single torch 32 and a single optical sensing system 34, in other embodiments there may be more than one torch or more than one optical sensing system.

Figure 2:
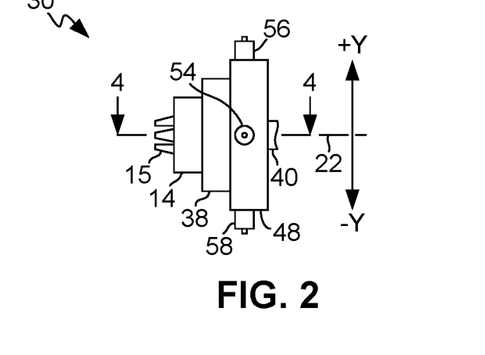
FIG. 2 is a side elevation view of a portion of the system of FIG. 1.
Figure 4:
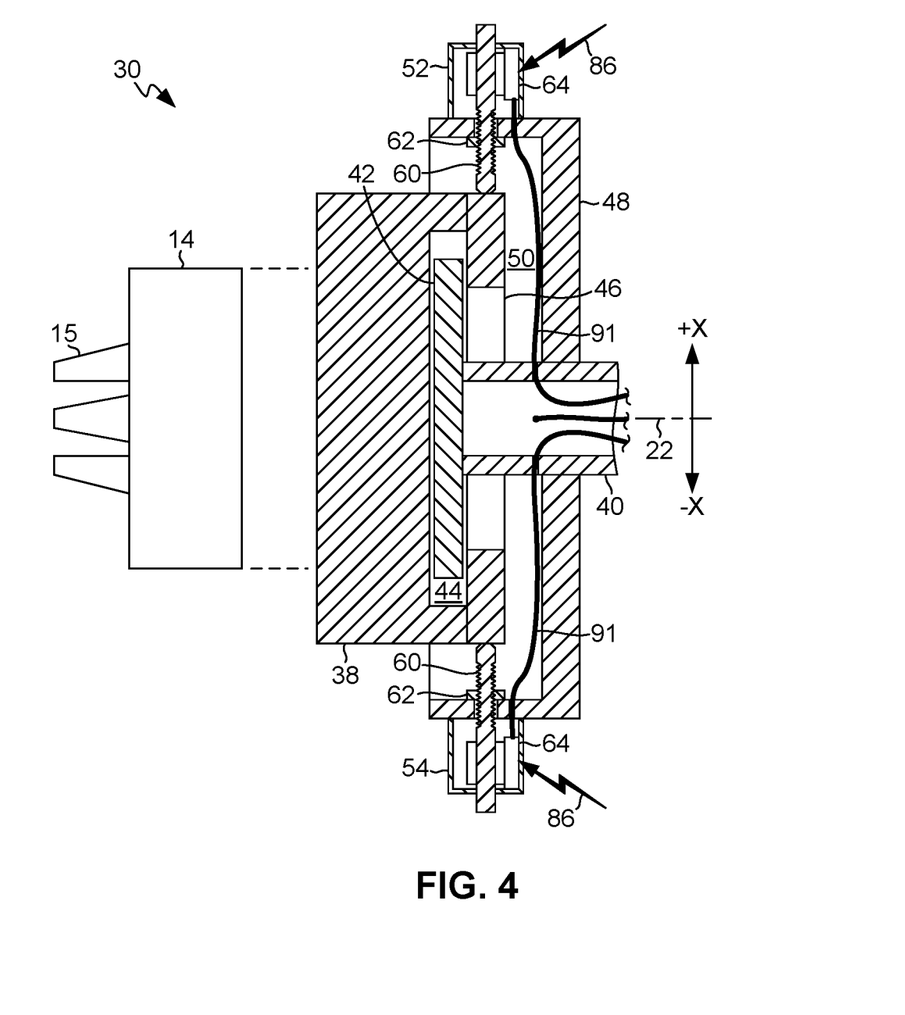
FIG. 4 is an exploded view, partially sectioned, with the section taken along line 4-4 of FIG. 2.

As illustrated in FIGS. 2 and 4, device 30 may include a body 38 coupled to an arm 40. Body 38 may be generally cylindrical in shape. Arm 40 likewise may be generally cylindrical or rod shaped. Arm 40 is configured to rotate about the above-described lathe axis 22. First chuck 14 is connected in fixed relation to body 38. As the internal structure of first chuck 14 may be conventional and well known to one of ordinary skill in the art, first chuck 14 is not shown in cross section in FIG. 4.

A slip joint is defined by the coupling between arm 40 and body 38 (and thus between arm 40 and first chuck 14). The slip joint is defined by the manner in which a pin 42, which is connected to an end of arm 40, is retained in a retaining cavity 44 in body 38. More specifically, in the illustrated embodiment, pin 42 and retaining cavity 44 are each cylindrical in shape, and pin 42 is slip fit within retaining cavity 44. That is, retaining cavity 44 has a width (dimension in the direction of lathe axis 22) that is just slightly greater than the width of pin 42, such that pin 42 can slide within retaining cavity 44 in two dimensions in a plane normal to lathe axis 22. The slip joint may be lubricated to reduce friction between pin 42 and the adjacent walls of retaining cavity 44.

Figure 3:
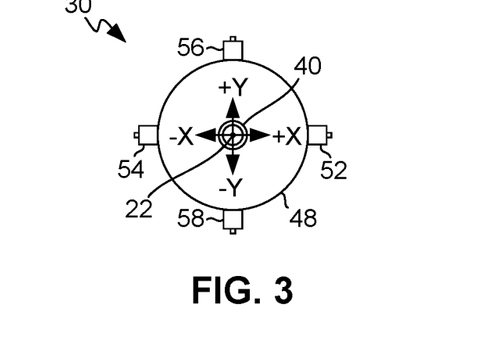
FIG. 3 is an end view of the device of FIG. 2.

As illustrated in FIG. 3, the above-referenced plane normal to lathe axis 22 may be described by a two-dimensional (X-Y) coordinate system. In FIG. 3, arrows indicate a positive X axis, a negative X axis, a positive Y axis, and a negative Y axis in an X-Y coordinate system that has lathe axis 22 at its origin. Note that pin 44 is free to move or slide with respect to retaining cavity 44 in any direction in a plane normal to lathe axis 22 (i.e., two dimensionally), and that such a direction may be defined using the X-Y coordinate system. Freedom of movement of pin 42 is limited or constrained by the spacing between the periphery of pin 44 and the walls of retaining cavity 44. As the shapes of pin 42 and retaining cavity 44 are cylindrical in the illustrated embodiment, freedom of movement of pin 42 in plane normal to lathe axis 22 is limited or constrained by the difference between the diameters of pin 42 and retaining cavity 44.

Referring again to FIG. 4, arm 40 extends from pin 42 through an opening 46 in body 38 to connect with tailstock 20. Opening 46 may have a diameter less than the diameter of pin 42 to capture or retain pin 42 within retaining cavity 44. Note that while pin 42 is free to move or slide with respect to body 38 in a plane normal to lathe axis 22, pin 42 is coupled essentially in fixed relation to body 38 with respect to lathe axis 22. Stated another way, the slip joint couples arm 40 and first chuck 14 in movable relation to each other with respect to a plane normal to lathe axis 22, yet couples arm 40 and first chuck 14 in fixed relation against axial motion relative to each other with respect to lathe axis 22 (and thus the first chuck axis of rotation). Accordingly, in operation, as described in further detail below, motion of arm 40 in an axial direction (i.e., along lathe axis 22) is transferred to body 38 and thus also transferred to first chuck 14.

Arm 40 also extends through a frame 48, which is connected in fixed relation to arm 40 and thus is configured to rotate with arm 40 about lathe axis 22. Frame 48 may be generally cylindrical and have a cup shape defined by an interior space 50. A portion of body 38 extends into interior space 50.

An actuator system comprising actuator motors 52, 54, 56, and 58 may be arranged at equidistant intervals about the periphery of frame 48 and thus, correspondingly, about the periphery of the portion of body 38 that extends into interior space 50. The actuator system is thus coupled to arm 40 via frame 48. Although in the illustrated embodiment there are four actuator motors 52-58, in other embodiments (not shown) there could be three actuator motors. Each of actuator motors 52-58 has a pushrod 60. A portion of each pushrod 60 is threaded. The threaded portion extends through a threaded nut or collar 62 in a wall of frame 48. Each of actuator motors 52-58 is individually controllable to rotate its pushrod 60 either clockwise or counterclockwise. The threaded collar 62 converts this rotary motion into linear motion. Accordingly, each of actuator motors 52-58 is individually controllable to extend its pushrod 60 toward body 38 or retract its pushrod 60 away from body 38. The distal end of a pushrod 60 may contact body 38. Extending a pushrod 60 thus can displace body 38 (and first chuck 14, which is connected in fixed relation to body 38) a controllable distance with respect to lathe axis 22. Each of actuator motors 52-58 may include a motor controller 64. Motor controller 64 is configured to receive control signals using a wireless (e.g., radio frequency, optical, etc.) communication link.

By extending its pushrod 60, actuator motor 54 can displace first chuck 14 in the positive X-axis direction. Similarly, by extending its pushrod 60, actuator motor 52 can displace first chuck 14 in the negative X-axis direction. Likewise, by extending its pushrod 60, actuator motor 58 can displace first chuck 14 in the positive Y-axis direction. And by extending its pushrod 60, actuator motor 56 can displace first chuck 14 in the negative Y-axis direction. When one or more of actuator motors 52-58 extend their pushrods 60, one or more others of actuator motors 52-58 may retract their pushrods by corresponding distances, so that the distal ends of all pushrods 60 remain in contact with body 38.

In a neutral position (e.g., FIG. 4), first chuck 14 is centered on lathe axis 22, and each of pushrods 60 is extended the same amount. In the neutral position, the distal end of each pushrod 60 is in contact with body 38. From the neutral position, each of pushrods 60 may be configured to be extendable and retractable a certain distance. That distance may be less than or equal to one-half the difference between the diameters of pin 42 and retaining cavity 44.

Figure 5:
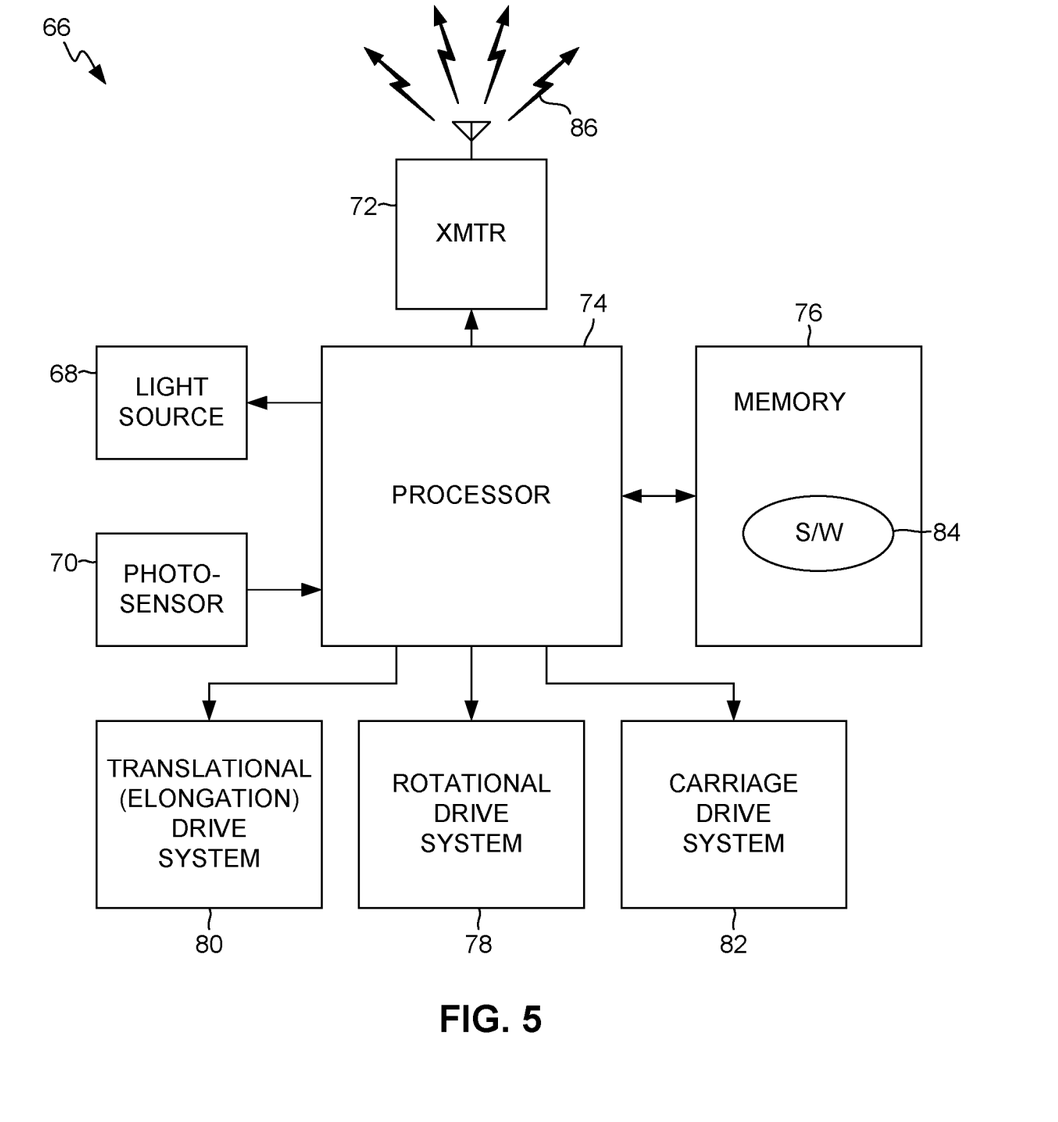
FIG. 5 is a block diagram of a control system for the system of FIG. 1.

As illustrated in FIG. 5, a control system 66 may include a light source 68, a photosensor 70, a wireless transmitter 72, a processor 74, a memory 76, a rotational drive system 78, a translational or elongation drive system 80, and a carriage drive system 82. Light source 68, photosensor 70, and a portion of other elements of control system 66 may be included in optical sensing system 34 (FIG. 1). Light source 68 may comprise a laser, and photosensor 70 may comprise a photodiode or other sensor configured to detect an optical signal. As described above with regard to FIG. 1, optical sensing system 34 may be configured to measure a displacement of a portion of glass core rod 12 from a reference point. For example, light source 68 and photosensor 70 may be positioned on opposite sides of lathe axis 22. Thus, the extent to which glass core rod 12 obstructs or attenuates the optical signal received by photosensor 70 represents the extent of displacement of glass core rod 12 from lathe axis 22. Although not shown in FIG. 1 for purposes of clarity, portions of control system 66 may be contained within base 24, carriage 36, headstock 18, or tailstock 20.

Processor 74 may be configured by software or firmware 84 stored in memory 76 to control the methods described below and otherwise control the operation of system 10 (FIG. 1). In other embodiments (not shown), the methods may be controlled by a programmable logic controller (PLC) or similar industrial control device instead of the combination of a more general-purpose processor and memory. Processor 74 may control wireless transmitter 72 to transmit control signals 86 to motor controllers 64 associated with actuator motors 52-58. The communication link or links over which control signals 86 are transmitted may be based on radio frequency (RF) communication, optical communication, or other technology. For example, the communication links may be Bluetooth. Processor 74 may, for example, compute a direction and magnitude (i.e., distance) in the X-Y coordinate system of motion to be applied to body 38. The direction and magnitude may be encoded in control signals 86. In response to such control information, actuator motors 52-58 two-dimensionally adjust the position of body 38 (and thus first chuck 14) in the manner described above.

Electrical power to actuator motors 52-58 may be provided through an endcap 88 (FIG. 1). Although not shown for purposes of clarity, brushes or a similar rotary electrical contact system in endcap 88 may be included to transfer the electrical power from power supply wires 90 to distribution wires 91 (FIG. 4) or similar conductors in device 30. Motor controllers 64 receive the electrical power from distribution wires 91 and receive control signals 86 via the wireless communication link with wireless transmitter 72. Based on the control information in control signals 86, motor controller 64 may apply electrical power in a controlled manner to actuator motors 52-58.

Processor 74 may also control rotational drive system 78 to rotate first and second chucks 14 and 16 at a controlled or selected speed. Processor 74 may further control elongation drive system 80 to move tailstock 20 in the manner described above at a controlled or selected speed. Processor 74 may further control carriage drive system 82 to move carriage 36 in the manner described above at a controlled or selected speed. Although not shown for purposes of clarity, rotational drive system 78 may include one or more motors and drive trains (e.g., gears, pulleys, etc.) that, in conjunction with features of device 30 described above, transfer rotational motion to first and second chucks 14 and 16. Similarly, elongation drive system 80 and carriage drive system 82 may include motors, etc.

Figure 6:
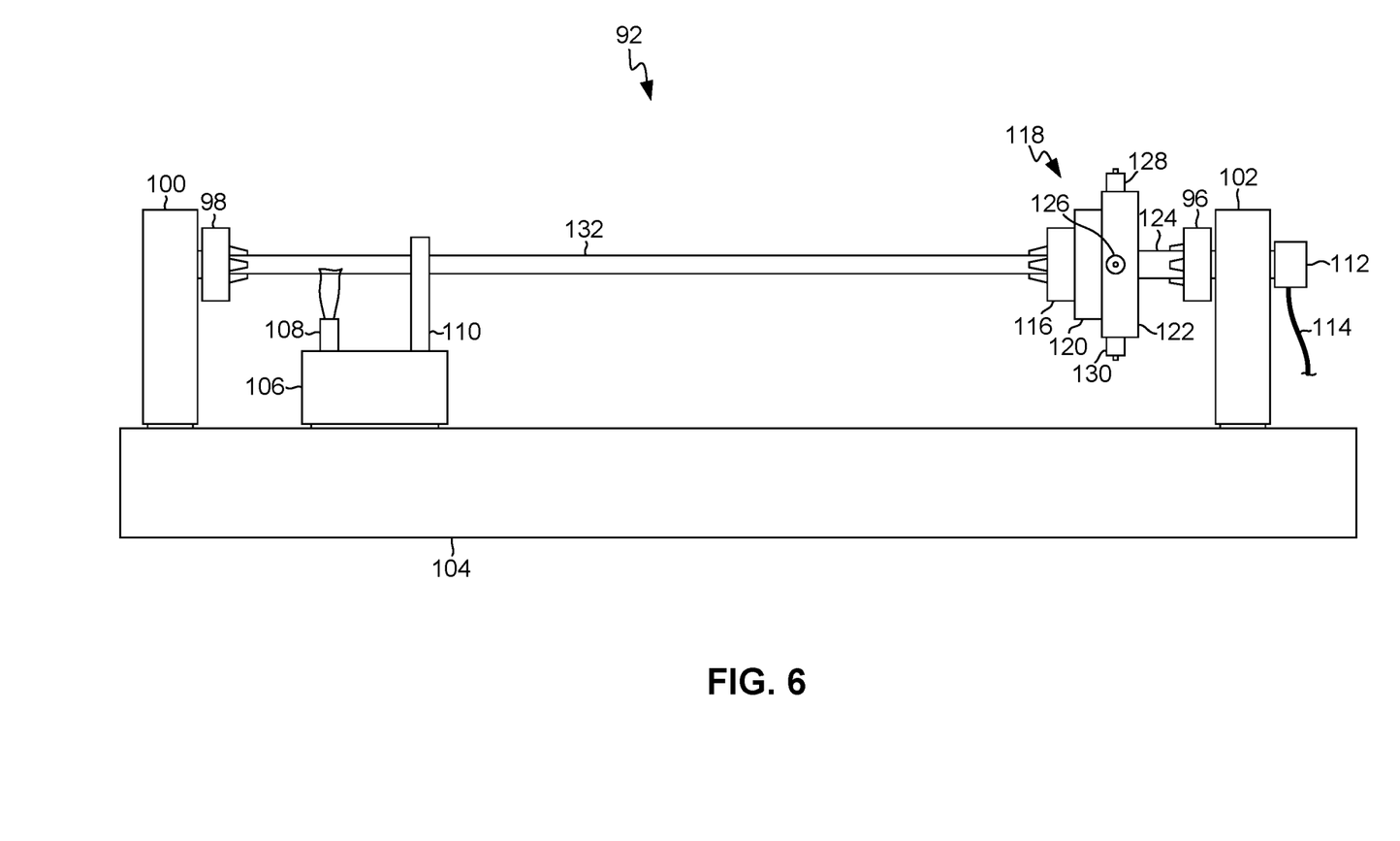
FIG. 6 is similar to FIG. 1, showing an alternative embodiment of the system.

As illustrated in FIG. 6, an alternative system 92 may be similar in some respects to above-described system 10. For example, system 92 may include a first lathe chuck 96, a second lathe chuck 98, a headstock 100, a tailstock 102, a base 104, a carriage 106, a torch 108, an optical sensing system 110, an endcap 112, wires 114, etc., which may be identical in structure and function to corresponding elements described above with regard to FIGS. 1-4. System 92 may include the above-described control system 66 (FIG. 5). System 92 is configured to operate in the same manner as above-described system 10 except for the manner in which a first device chuck 116 of a device 118 is coupled to tailstock 102. In addition to first device chuck 116, device 118 includes a body 120, a frame 122, an arm 124, and actuator motors 126, 128, 130, etc., which may be identical in structure and function to corresponding elements described above with regard to FIGS. 1-4. However, the end of arm 124 is not directly connected to tailstock 20 but rather is coupled to tailstock 20 by being retained in first lathe chuck 96. In system 92, first device chuck 116 is configured to retain a first end of a glass core rod 132, and second lathe chuck 98 is configured to retain a second end of glass core rod 132. Conveniently, system 92 may be provided by retrofitting with device 118 a conventional lathe of a type used for elongating glass core rods, the above-described control system 66, and related features.

Figure 7:
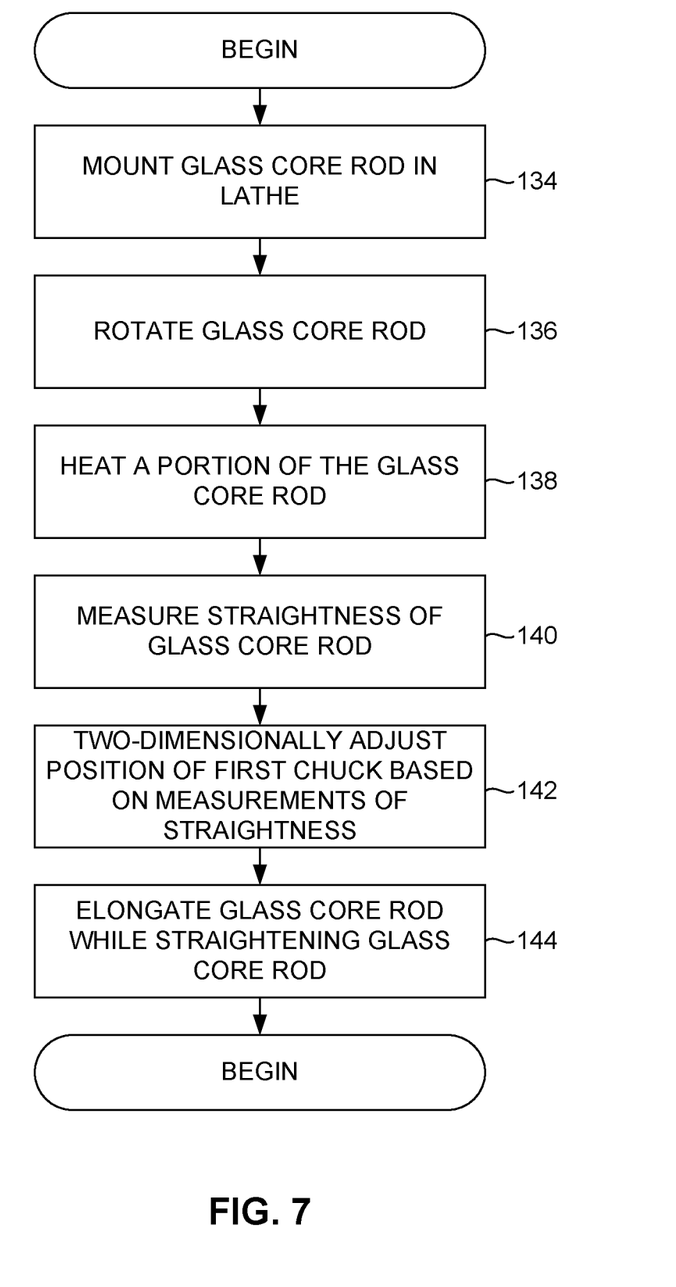
FIG. 7 is a flow diagram illustrating an exemplary method for straightening and elongating a glass core rod.

As illustrated in FIG. 7, an exemplary method for straightening and elongating a glass core rod may use above-described system 10, system 92, or a similar system. The method may be controlled by processor 74 being programmed or otherwise configured with software or firmware 84 (FIG. 5). Although certain acts or steps in the method naturally precede others for the exemplary embodiments to operate as described, the invention is not limited to the order of those acts or steps if such order or sequence does not alter the functionality of the invention. That is, it is recognized that some acts or steps may be performed before, after, or in parallel (i.e., substantially simultaneously) with other acts or steps without departing from the scope and spirit of the invention. In some instances, certain acts or steps may be omitted or not performed, without departing from the scope and spirit of the invention. Further, words such as "thereafter," "then," "next," etc., are not intended to limit the order of the acts or steps. Rather, such words are used to aid in guiding the reader through the description of an exemplary method.

As indicated by block 134, an operator may mount a glass core rod in the system. For example, first and second ends of the rod may be mounted in the first and second chucks, respectively. The first chuck may be the above-described first chuck 14 (FIG. 1) or first device chuck 116 (FIG. 6), which are movable in the manner described above.

As indicated by block 136, the system may rotate the glass core rod. As described above, the system can control the speed of rotation of the glass core rod. As indicated by block 138, the torch or similar heat generator may heat a portion of the glass core rod. As described above, the system may control when the heat is applied (or not applied), the amount of heat applied and, by controlling movement of the torch, to what portion of the glass core rod the heat is applied. Mounted on a carriage, the torch may continuously move along the glass core rod. The speed of the torch may be controlled. Such control parameters may be determined by the processor using an algorithm embodied in the software.

As indicated by block 140, the system may measure straightness of the glass core rod using the optical sensing system. The system may move the optical sensing system along a path that traverses the length of the glass core rod, obtaining displacement measurements at various points along the path. The collected displacement measurements may be expected to vary from each other within a tolerance amount if the glass core rod is straight. The collected displacement measurements may be expected to vary from each other by greater amounts if the glass core rod is not straight. The collected displacement measurements may describe a profile of the glass core rod, such as a bowed shape. The extent and shape of the curvature of the glass core rod is bowed can be used to determine at what points on the glass core rod to apply displacement forces. The displacement forces may also be applied continuously based on bow calculated over each rotation of the glass core rod.

The measurements may be obtained while the glass core rod is rotated and while the torch heats the glass core rod and advances along the glass core rod, in a continuous process. As the optical sensing system may be mounted on the carriage along with the torch, the optical sensing system may obtain a measurement a fixed distance in advance of the torch. The displacement measurements may comprise an input to the algorithm. The processor, in accordance with the algorithm, may determine a magnitude and direction of a bow in the glass core rod.

As indicated by block 142, the processor, in accordance with the algorithm, and based on the magnitude and direction of a bow in the glass core rod, may determine a position (with respect to a plane normal to the lathe axis of rotation) to which the first end of the glass core rod is to be two-dimensionally moved or displaced. The processor provides corresponding control signals to the actuator system (motors) to two-dimensionally move the first chuck. The heated portion of the glass core rod bends or otherwise deforms in compliance with the displacement of the first end of the glass core rod in the first chuck. The system may continue to adjust the position of the first chuck in this manner while the glass core rod is rotated and while the torch heats the glass core rod and advances along the glass core rod, in a continuous process.

As indicated by block 144, the system may elongate the glass core rod by activating the elongation drive system while the torch heats a portion of the glass core rod. As described above, the elongation drive system advances the tailstock, to which the first chuck is coupled via the arm and the slip joint. That is, translational motion of the tailstock is transferred to the first chuck via the arm and the slip joint. Note that although the first chuck is movable with respect to the arm in a plane normal to the lathe axis of rotation, the first chuck is essentially not movable with respect to the arm in directions along the lathe axis of rotation. The system may continue to elongate the glass core rod while the torch heats the glass core rod, while the glass core rod is rotated, while displacement measurements are obtained, and while adjusting the position of the first chuck, in a continuous process.

One or more illustrative or exemplary embodiments of the invention have been described above. However, it is to be understood that the invention is defined by the appended claims and is not limited to the specific embodiments described.

What is claimed is:

1. A system, comprising:
    a first chuck having a first chuck axis of rotation and configured to retain a first end of a glass core rod in an orientation wherein a longitudinal axis of the glass core rod is substantially aligned with the first chuck axis of rotation;
    an arm having an arm axis substantially aligned with the first chuck axis of rotation;
    a slip joint coupling the arm and the first chuck in fixed relation against relative axial motion with respect to the first chuck axis of rotation and connecting the arm and the first chuck in two-dimensionally movable relation with respect to a plane normal to the first chuck axis of rotation;
    an actuator system coupled to the arm and configured to two-dimensionally adjust a position of the first chuck in the plane; and
    a control system having an optical sensing system configured to measure straightness of the glass core rod, the control system configured to control the actuator system in response to optical measurements of the straightness of the glass core rod.

2. The system of claim 1, wherein the slip joint comprises a body fixedly connected to the first chuck, a retaining cavity in the body having a cavity diameter in the plane, and a pin in the cavity having a pin diameter in the plane less than the cavity diameter, the arm extending from the pin through an opening in the body having an opening diameter less than the cavity diameter and less than the pin diameter.

3. The system of claim 2, wherein:
the retaining cavity has a cylindrical shape; and
the pin has a cylindrical shape.

4. The system of claim 3, wherein the actuator system comprises:
a frame connected to the arm; and
at least three actuator motors spaced at equidistant intervals about a periphery of the body, each actuator motor having a pushrod controllably extendable to displace the body a controllable distance with respect to the lathe axis of rotation.

5. The system of claim 4, wherein the pushrod comprises a threaded rod extendable in response to rotation of a corresponding actuator motor.

6. The system of claim 5, wherein the frame has a cylindrical cup shape, and the at least three actuator motors are mounted to the frame.

7. The system of claim 1, further comprising a torch configured to traverse a path parallel to the first chuck axis of rotation.

8. The system of claim 7, wherein the torch and the optical sensing system are mounted on a carriage.

9. The system of claim 1, wherein the optical sensing system comprises a laser and a photosensor, the laser configured to direct a beam toward the glass core rod, the photosensor configured to receive a beam partially obstructed by the glass core rod.

10. The system of claim 1, further comprising an elongation lathe having a first lathe chuck rotatably mounted with respect to a lathe axis of rotation, a second lathe chuck rotatably mounted with respect to the lathe axis of rotation, a rotational drive system, and an elongation drive system, the first lathe chuck configured to retain an end of the arm, the second lathe chuck configured to retain a second end of the glass core rod, the rotational drive system configured to rotate the first and second lathe chucks, the elongation drive system configured to translate the first lathe chuck along the lathe axis of rotation.

11. A system, comprising:
a lathe having a first chuck and a second chuck each rotatably mounted with respect to a lathe axis of rotation, the first chuck configured to retain a first end of a glass core rod, the second chuck configured to retain a second end of the glass core rod, a rotational drive system configured to rotate the second chuck;
an arm having an arm axis substantially aligned with the lathe axis of rotation;
a slip joint coupling the arm and the first chuck in fixed relation against relative axial motion with respect to the lathe axis of rotation and connecting the arm and the first chuck in two-dimensionally movable relation with respect to a plane normal to the lathe axis of rotation;
an elongation drive system coupled to the arm and configured to translate the first chuck along the lathe axis of rotation via the slip joint;

an actuator system coupled to the arm and configured to two-dimensionally adjust a position of the first chuck in the plane via the slip joint; and
a control system having an optical sensing system configured to measure straightness of the glass core rod, the control system configured to control the actuator system in response to optical measurements of the straightness of the glass core rod.

12. The system of claim 11, wherein the slip joint comprises a body fixedly connected to the first chuck, a retaining cavity in the body having a cavity diameter in the plane, and a pin in the cavity having a pin diameter in the plane less than the cavity diameter, the arm extending from the pin through an opening in the body having an opening diameter less than the cavity diameter and less than the pin diameter.

13. The system of claim 12, wherein:
the retaining cavity has a cylindrical shape; and
the pin has a cylindrical shape.

14. The system of claim 13, wherein the actuator system comprises:
a frame connected to the arm; and
at least three actuator motors spaced at equidistant intervals about a periphery of the body, each actuator motor having a pushrod controllably extendable to displace the body a controllable distance with respect to the lathe axis of rotation.

15. The system of claim 14, wherein the pushrod comprises a threaded rod extendable in response to rotation of a corresponding actuator motor.

16. The system of claim 15, wherein the frame has a cylindrical cup shape, and the at least three actuator motors are mounted to the frame.

17. The system of claim 11, further comprising a torch configured to traverse a path parallel to the lathe axis of rotation.

18. The system of claim 11, wherein the torch and the optical sensing system are mounted on a carriage.

19. The system of claim 11, wherein the optical sensing system comprises a laser and an optical sensor, the laser configured to direct a beam toward the glass core rod, the optical sensor configured to receive a beam partially obstructed by the glass core rod.

20. A method, comprising:
mounting a glass core rod in a lathe by retaining a first end of the glass core rod in a first chuck rotatably mounted with respect to a lathe axis of rotation and a second end of the glass core rod in a second chuck rotatably mounted with respect to the lathe axis of rotation;
rotating the glass core rod in the lathe;
measuring straightness of the glass core rod using an optical sensing system;
heating a portion of the glass core rod;
two-dimensionally adjusting a position of the first chuck in a plane normal to the lathe axis of rotation using an actuator system and a control system responsive to measurements received from the optical sensing system; and
elongating the glass core rod using an elongation drive system substantially simultaneously with two-dimensionally adjusting the position of the first chuck, wherein a slip joint transfers axial motion produced by the elongation drive system to the first chuck while the first chuck is rotating.

21. The method of claim 20, wherein the actuator system adjusts the position of the first chuck using at least three actuator motors spaced at equidistant intervals about a periphery of the first chuck, each actuator motor having a pushrod controllably extendable to displace the first chuck a controllable distance with respect to the lathe axis of rotation.

* * * * *